(12) United States Patent
Hatakeyama et al.

(10) Patent No.: US 7,528,279 B2
(45) Date of Patent: May 5, 2009

(54) ADAMANTANE DERIVATIVES AND PROCESS FOR PRODUCING THE SAME

(75) Inventors: Naoyoshi Hatakeyama, Chiba (JP); Shinji Tanaka, Chiba (JP); Hidetoshi Ono, Chiba (JP); Yasunari Okada, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 10/588,080

(22) PCT Filed: Feb. 1, 2005

(86) PCT No.: PCT/JP2005/001404

§ 371 (c)(1),
(2), (4) Date: Jan. 10, 2007

(87) PCT Pub. No.: WO2005/075406

PCT Pub. Date: Aug. 18, 2005

(65) Prior Publication Data

US 2007/0129532 A1 Jun. 7, 2007

(30) Foreign Application Priority Data

| Feb. 5, 2004 | (JP) | 2004-029034 |
| Mar. 10, 2004 | (JP) | 2004-066626 |
| Jul. 27, 2004 | (JP) | 2004-218686 |
| Oct. 8, 2004 | (JP) | 2004-296542 |

(51) Int. Cl.
*C07C 69/54* (2006.01)
*C07C 67/29* (2006.01)
*C07C 303/28* (2006.01)
*C07C 303/44* (2006.01)
*C07C 309/66* (2006.01)

(52) U.S. Cl. ...................... 560/220; 560/222

(58) Field of Classification Search .................. None
See application file for complete search history.

(56) References Cited

FOREIGN PATENT DOCUMENTS

| EP | 0 999 474 A1 | 5/2000 |
| EP | 1 577 285 A1 | 9/2005 |
| EP | 1 803 708 A1 | 7/2007 |
| JP | 2000 122295 | 4/2000 |
| JP | 2001 048931 | 2/2001 |
| JP | 2001 240625 | 9/2001 |
| WO | WO 03/104182 A1 | 12/2003 |

OTHER PUBLICATIONS

U.S. Appl. No. 11/575,555, filed Mar. 19, 2007, Hatakeyama et al.
U.S. Appl. No. 10/588,080, filed Jan. 10, 2007, Hatakeyama et al.

*Primary Examiner*—Daniel M Sullivan
*Assistant Examiner*—Yevegeny Valenrod
(74) *Attorney, Agent, or Firm*—Oblon, Spivak, McClelland, Maier & Neustadt, P.C.

(57) ABSTRACT

The present invention provides an adamantane derivative (I) having a structure represented by the general formula (I); an adamantane derivative (II) having a structure represented by the general formula (II); and a process for producing those adamantane derivatives. An alcohol form of an adamantane compound is reacted with a sulfonyl compound to obtain the adamantane derivative (II), which is then reacted with an alcohol to obtain the adamantane derivative (I). The adamantane derivative (I) and adamantane derivative (II) each having the structure represented by the general formula (I) and general formula (II), respectively, is a novel adamantyl(meth)acrylate compound and useful as a monomer for functional resins such as a photosensitive resin in the field of photolithography.

[Chemical formula 1] (I)

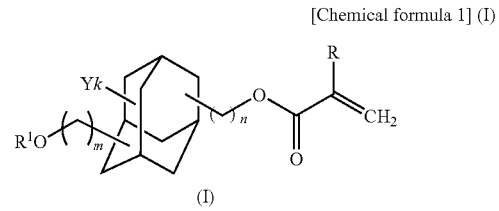

[Chemical formula 2] (II)

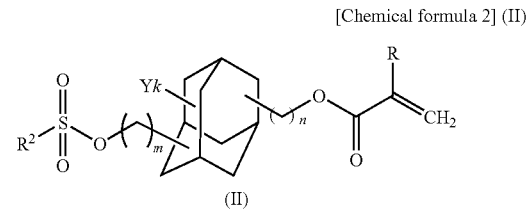

7 Claims, No Drawings

ADAMANTANE DERIVATIVES AND PROCESS FOR PRODUCING THE SAME

TECHNICAL FIELD

The present invention relates to a novel adamantane derivative and a process for producing the same. More specifically, the present invention relates to novel alkoxy group-substituted adamantyl (meth)acrylates and alkylsulfonyloxy-substituted adamantyl (meth)acrylates useful as monomers for functional resins such as a photosensitive resin in the field of photolithography, and a process for producing each of those adamantane derivatives efficiently.

BACKGROUND ART

Adamantane has a structure in which four cyclohexane rings are condensed in a cage fashion, and is a compound which has high symmetry and is stable. A derivative of adamantane is known to be useful as, for example, a raw material for a drug or a raw material for a high functionally industrial material because the derivative shows a specific function. Attempts have been made to use the derivative in an optical disk substrate, an optical fiber, a lens, or the like because the derivative has, for example, optical properties and heat resistance (Patent Document 1 and Patent Document 2).

In addition, attempts have been made to use adamantane esters as raw materials for resins for photoresist by utilizing the acid sensitivity, resistance to dry etching, permeability to ultraviolet light, and the like of the adamantane esters (Patent Document 3).

Meanwhile, the miniaturization of a semiconductor device has progressed in recent years. In association with the progress, additional miniaturization has been demanded in a lithography step in the production of the semiconductor device. Therefore, investigation has been conducted into various methods of forming a fine pattern by using a photoresist material corresponding to light to be applied having a short wavelength such as KrF, ArF, or $F_2$ excimer laser light. In addition, the appearance of a new photoresist material capable of corresponding to light to be applied having a short wavelength such as the above-mentioned excimer laser light is desired. A monomer into which a hydroxyl group is introduced for improving the adhesiveness of a silicon substrate has been conventionally known (Patent Document 4). A photoresist material having a functionally functional group that has not been known heretofore is desired.

Patent Document 1: Japanese Patent Application Laid-Open No. Heisei 6(1994)-305044
Patent Document 2: Japanese Patent Application Laid-Open No. Heisei (1997)-302077
Patent Document 3: Japanese Patent Application Laid-Open No. Heisei 4(1992)-39665
Patent Document 4: Japanese Patent Application Laid-Open No. Showa 63(1988)-33350

DISCLOSURE OF THE INVENTION

The present invention has been made under such circumstances, and an object of the present invention is to provide a novel adamantane derivative useful as a monomer for a functional resin such as a photo sensitive resin in the field of photolithography, and a process for producing the same.

The inventors of the present invention have made extensive studies with a view to achieving the above object. As a result, they have found that alkoxy-substituted adamantyl (meth)acrylates and methanesulfonyloxy-substituted adamantyl (meth)acrylates each having a specific structure are novel compounds and are suitable for the object, and that each of these compounds can be efficiently produced by reacting an alcohol form having a corresponding adamantyl group as a raw material.

The present invention has been completed on the basis of such findings.

That is, the present invention provides the following adamantane derivatives and a process for producing the same.

[1] An adamantane derivative, characterized by comprising a structure represented by a general formula (I):

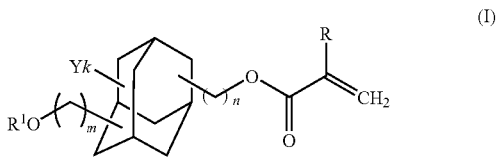

(I)

where R represents a hydrogen atom, a methyl group, or a $CF_3$ group, Ys each represent an alkyl group having 1 to 10 carbon atoms, a halogen atom, or a hydroxyl group, or two Ys are coupled to form =O, and multiple Ys may be identical to or different from each other, $R^1$ represents an alkyl group or a cycloalkyl group having 1 to 10 carbon atoms, and may contain a hetero atom and/or a nitrile group in part of its structure, k represents an integer of 0 to 14, and m and n each independently represent an integer of 0 to 4.

[2] An adamantane derivative according to the above item [1], in which a substituent except Ys is present at a bridge head position.

[3] An adamantane derivative according to the above item [1] or [2], in which $R^1$ represents a group having tertiary carbon adjacent to O.

[4] An adamantane derivative, characterized by comprising a structure represented by a general formula (II):

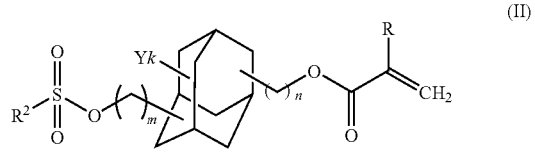

(II)

where R represents a hydrogen atom, a methyl group, or a $CF_3$ group, $R^2$ represents an alkyl group having 1 to 10 carbon atoms, a phenyl group, an alkylphenyl group, or a $CF_3$ group, Ys each represent an alkyl group having 1 to 10 carbon atoms, a halogen atom, or a hydroxyl group, or two Ys are coupled to form =O, and multiple Ys may be identical to or different from each other, k represents an integer of 0 to 14, and m and n each independently represent an integer of 0 to 4.

[5] An adamantane derivative according to the above item [4], in which $R^2$ represents a methyl group.

[6] A process for producing an adamantane derivative having a structure represented by the general formula (II):

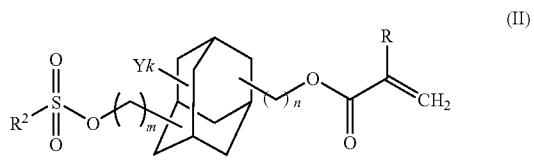

where R represents a hydrogen atom, a methyl group, or a $CF_3$ group, $R^2$ represents an alkyl group having 1 to 10 carbon atoms, a phenyl group, an alkylphenyl group, or a $CF_3$ group, Ys each represent an alkyl group having 1 to 10 carbon atoms, a halogen atom, or a hydroxyl group, or two Ys are coupled to form =O, and multiple Ys may be identical to or different from each other, k represents an integer of 0 to 14, and m and n each independently represent an integer of 0 to 4, the process being characterized by comprising reacting an alcohol form of an adamantane compound represented by a general formula (III):

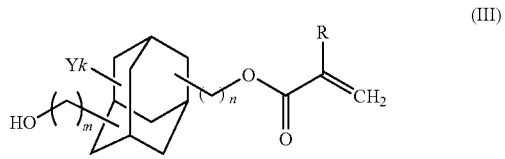

where R, Ys, k, m, and n each have the same meaning as that described above, with a sulfonyl compound represented by a general formula (IV):

where $R^2$ represents an alkyl group having 1 to 10 carbon atoms, a phenyl group, an alkylphenyl group, or a $CF_3$ group, and X represents a hydroxyl group or a halogen atom.

[7] A process for producing an adamantane derivative according to the above item [6], in which the alcohol form of the adamantane compound represented by the general formula (III) and the sulfonyl compound represented by the general formula (IV) are reacted with each other in an organic solvent having a dielectric constant at 20° C. of 8 or less.

[8] A process for producing an adamantane derivative according to the above item [6] or [7], in which the sulfonyl compound represented by the general formula (IV) comprises methanesulfonyl halide.

[9] A process for producing an adamantane derivative according to any one of the above item [6] to [8], in which, after the alcohol form of the adamantane compound represented by the general formula (III) and the sulfonyl compound represented by the general formula (IV) have been reacted with each other, a reaction product is separated from a liquid after completion of the reaction, a poor solvent for a by-product polymer in the reaction product is added to the reaction product, and a precipitate of the by-product polymer to be produced is removed.

[10] A process for producing an adamantane derivative according to the above item [9], in which the poor solvent for the by-product polymer comprises methanol.

[11] A process for producing an adamantane derivative represented by the general formula (I):

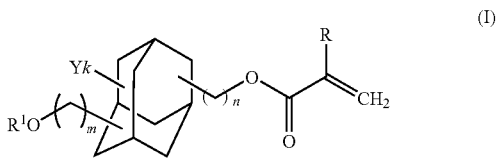

where R represents a hydrogen atom, a methyl group, or a $CF_3$ group, Ys each represent an alkyl group having 1 to 10 carbon atoms, a halogen atom, or a hydroxyl group, or two Ys are coupled to form =O, and multiple Ys may be identical to or different from each other, $R^1$ represents an alkyl group or a cycloalkyl group having 1 to 10 carbon atoms, and may contain a hetero atom and/or a nitrile group in part of its structure, k represents an integer of 0 to 14, and m and n each independently represent an integer of 0 to 4, the process being characterized by comprising reacting an adamantane derivative represented by the general formula (II):

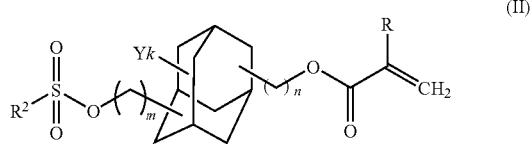

where $R^2$ represents an alkyl group having 1 to 10 carbon atoms, a phenyl group, an alkylphenyl group, or a $CF_3$ group, R, Ys, k, m, and n each have the same meaning as that described above, with an alcohol.

[12] A process producing an adamantane derivative according to the above item (11), in which 3-methanesulfonyloxy-1-adamantyl(meth)acrylate is reacted with the alcohol.

[13] A process for producing an adamantane derivative according to the above item (11) or (12), in which the alcohol comprises a tertiary alcohol.

BEST MODE FOR CARRYING OUT THE INVENTION

Hereinafter, a compound represented by a general formula (I) of the present invention is represented as an adamantane derivative (I), and a compound represented by a general formula (II) of the present invention is represented as an adamantane derivative (II). Each of those adamantane derivatives is a novel compound.

Next, those adamantane derivatives and a process for producing each of them will be described.

First, the adamantane derivative (I) of the present invention is one of the alkoxy group-substituted adamantyl(meth)acrylates each having a structure represented by the general formula (I).

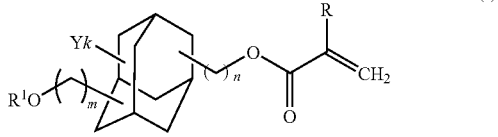

(I)

In the general formula (I), R represents a hydrogen atom, a methyl group, or a trifluoromethyl group, Ys each represent an alkyl group having 1 to 10 carbon atoms, a halogen atom, or a hydroxyl group, or two Ys are coupled to form =O. Multiple Ys may be identical to or different from each other. $R^1$ represents an alkyl group having 1 to 10 carbon atoms, and may contain a hetero atom and/or a nitrile group in part of its structure. k represents an integer of 0 to 14, and m and n each independently represent an integer of 0 or more, or preferably 0 or 1. When m represents 0 and n represents 0, a structure in which oxygen is directly bound to an adamantyl group is shown.

Examples of an alkyl group having 1 to 10 carbon atoms in each of Ys and $R^1$ in the foregoing include a methyl group, an ethyl group, various propyl groups, various butyl groups, various pentyl groups, various hexyl groups, various heptyl groups, various octyl groups, various nonyl groups, and various decyl groups. Each of those groups may be linear or branched. The alkyl group may be substituted by a halogen atom, a hydroxyl group, or the like. In addition, $R^1$ represents a cycloalkyl group as well. When the alkyl group or cycloalkyl group represented by $R^1$ contains a hetero atom and/or a nitrile group in part of its structure, irregularities appearing on the side surface of a resist pattern are additionally alleviated when the derivative is used as a photosensitive resin.

Specific examples of $R^1$ may include the followings. Examples of $R^1$ bound with a primary carbon include a methyl group, ethyl group, 1-propyl group, 1-butyl group, 1-pentyl group, 3-methyl-1-butyl group, 2-methyl-1-butyl group, 2,2-dimethyl-1-butyl group, 3,3-dimethyl-1-butyl group, cyclohexylmethyl group, 1-adamantylmethyl group, 3-hydroxymethyl-1-adamantylmethyl group, 2-hydroxy-1-ethyl group, 2,3-bishydroxypropyl group, 2,2,2-tris(hydroxymethyl)-ethyl group, and 2-chloro-1-ethyl group.

Examples of $R^1$ bound with a secondary carbon include a 2-propyl group, 2-butyl group, 2-pentyl group, 3-methyl-2-butyl group, 3,3-dimethyl-2-butyl group, cyclohexyl group, 2-adamantyl group, 4-oxo-2-adamantyl group, 1-methoxy-2-propyl group, and 1,3-dihydroxy-2-propyl group.

Examples of $R^1$ bound with a tertiary carbon include a 2-methyl-2-propyl group (tert-butyl group), 2-methyl-2-butyl group (tert-pentyl group), 2,3-dimethyl-2-butyl group (tert-hexyl group) 1-adamantyl group, 3-hydroxy-1-adamantyl group, 4-oxo-1-adamantyl group, perfluoro-1-adamantyl group, perfluoro-3-hydroxy-1-adamantyl group, 1-methylcyclohexyl group, 1-ethylcyclopentyl group, and 2-methyl-2-adamantyl group.

$R^1$ preferably represents a group having tertiary carbon adjacent to O from the viewpoint of usefulness of the derivative as a novel substance. Of those, $R^1$ preferably represents a tert-butyl group, a tert-pentyl group, or a tert-hexyl group. In addition, a substituent except Ys is preferably present at a bridge head position.

Examples of a halogen atom in each of Ys include fluorine, chlorine, bromine, and iodine.

Examples of particularly preferable compounds represented by the above-mentioned general formula (I) include 3-tert-pentyloxy-1-adamantyl methacrylate, 3-tert-butyloxy-1-adamantyl acrylate, 3-tert-pentyloxy-1-adamantyl 2-trifluoromethyl acrylate, 3-tert-hexyloxy-1-adamantyl methacrylate, 3-tert-pentyloxymethyl-1-adamantylmethyl methacrylate, 3-tert-butyloxymethyl-1-adamantylmethyl acylate, 3-tert-pentyloxymethyl-1-adamantylmethyl 2-trifluoromethyl acrylate, 3-tert-butyloxy-perfluoro-1-adamantylmethacrylate, and 3-tert-pentyloxy-perfluoro-1-adamantyl acrylate.

Next, the adamantane derivative (II) will be described. The adamantane derivative (II) of the present invention is one of the sulfonyloxy-substituted adamantyl(meth)acrylates each having a structure represented by the general formula (II).

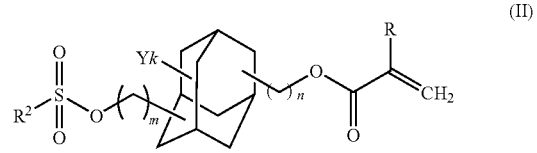

(II)

In the general formula (II), R represents a hydrogen atom, a methyl group, or a $CF_3$ group, $R^2$ represents an alkyl group having 1 to 10 carbon atoms, a phenyl group, an alkylphenyl group, or a $CF_3$ group, Ys each represent an alkyl group having 1 to 10 carbon atoms, a halogen atom, or a hydroxyl group, or two Ys are coupled to form =O. Multiple Ys may be identical to or different from each other. k represents an integer of 0 to 14, and m and n each independently represent an integer of 0 to 4. When m represents 0 and n represents 0, a structure in which oxygen is directly bound to an adamantyl group is shown.

Examples of an alkyl group having 1 to 10 carbon atoms in $R^2$ in the foregoing include those described above. Examples of an alkylphenyl group include a methylphenyl group, an ethylphenyl group, and a propylphenyl group.

Examples of adamantane derivatives (II) represented by the above-mentioned general formula (II) preferably include, as those in each of which $R^2$ represents a methyl group, 3-methanesulfonyloxy-1-adamantyl methacrylate, 3-methanesulfonyloxy-1-adamantyl acylate, 3-methanesulfonyloxy-1-adamantyl 2-trifluoromethyl acrylate, 1-methanesulfonyloxy-4-adamantyl methacrylate, 1-methanesulfonyloxy-4-adamantyl acrylate, 1-methanesulfonyloxy-4-adamantyl 2-trifluoromethyl acrylate, 3-methanesulfonyloxymethyl-1-adamantylmethyl methacrylate, 3-methanesulfonyloxymethyl-1-adamantylmethyl acrylate, 3-methanesulfonyloxymethyl-1-adamantylmethyl 2-trifluoromethyl acrylate, 3-methanesulfonyloxy-perfluoro-1-adamantyl methacrylate, and 3-methanesulfonyloxy-perfluoro-1-adamantyl acrylate.

Next, a preferable process for producing each of the adamantane derivative (I) and the adamantane derivative (II) will be described.

First, the adamantane derivative (II) is produced by reacting an alcohol form of an adamantane compound represented by the general formula (III) with a sulfonyl compound represented by the general formula (IV).

Examples of an alcohol of the adamantane compound represented by the general formula (III) as a raw material include hydroxy group-containing adamantyl(meth)acrylates such as a 3-hydroxy-1-adamantylmethacrylate, 3-hydroxy-1-adamantyl acylate, 3-hydroxy-1-adamantyl 2-trifluoromethyl acrylate, 3-hydroxymethyl-1-adamantylmethyl methacrylate, 3-hydroxymethyl-1-adamantylmethyl acrylate, 3-hydroxymethyl-1-adamantylmethyl 2-trifluoromethyl acrylate, 3-hydroxy-perfluoro-1-adamantyl methacrylate, and 3-hydroxy-perfluoro-1-adamantyl acrylate.

Next, in the sulfonyl compound represented by the general formula (IV), X preferably represents a halogen atom rather than a hydroxyl group from the viewpoint of reactivity, and particularly preferably represents a chlorine atom from an industrial viewpoint. Examples of the sulfonyl compound include methanesulfonyl chloride, ethanesulfonyl chloride, propanensulfonyl chloride, p-toluenesulfonyl chloride, and trifluoromethanesulfonyl chloride. Of those, methanesulfonyl chloride is preferable.

A charge ratio between the alcohol form of the adamantane compound represented by the general formula (III) and the sulfonyl compound represented by the general formula (IV) is preferably such that the sulfonyl compound is charged in an amount in the range of 1 to 1.5 mol with respect to 1 mol of the adamantane compound.

In this reaction, a base is generally used as a catalyst, and a solvent is used as required.

Examples of the base include: sodium amide; triethylamine; tributylamine; trioctylamine; pyridine; N,N-dimethylaniline; 1,5-diazabicyclo[4.3.0]nonene-5(DBN); 1,8-diazabicyclo[5.4.0]undecene-7(DBU); sodium hydroxide; potassium hydroxide; sodium hydride; potassium carbonate; silver oxide; sodium methoxide; and potassium t-butoxide. One kind of those catalysts may be used alone, or two or more kinds of them may be used in combination.

In this reaction, a solvent is ordinarily used. A solvent having a solubility for each of hydroxyl group-containing adamantyl(meth)acrylates as raw materials of 0.5 mass % or more, or desirably 5 mass % or more at a reaction temperature is preferably used as the solvent. The amount of the solvent is such that the concentration of the hydroxyl group-containing adamantyl(meth)acrylates in a reaction mixture is 0.5 mass % or more, or desirably 5 mass % or more. At this time, the adamantane derivative (II), which may be in a suspended state, is desirably dissolved. In addition, moisture in the solvent is desirably removed before use. Specific examples of the solvent include: hydrocarbon-based solvents such as n-hexane and n-heptane; ether-based solvents such as diethyl ether and tetrahydrofuran; halogen-based solvents such as dichloromethane and carbon tetrachloride; dimethylsulfoxide; and N,N-dimethylsulfoxide. One kind of those solvents may be used alone, or two or more kinds of them may be used as a mixture.

Of those, an organic solvent having a dielectric constant at 20° C. of 8 or less is preferably used as the solvent. The use of such solvent having a low dielectric constant can not only produce the target adamantane derivative (II) in high yield but also suppress the production of a polymer, thereby resulting in an improvement in handleability. Specific examples of such solvent include: hydrocarbon-based solvents such as toluene, n-hexane, n-heptane, and cyclohexane; ester-based solvents such as ethyl acetate; and mixed solvents of these solvents and ether-based solvents such as diethyl ether and tetrahydrofuran. One kind of those solvents may be used alone, or two or more kinds of them may be used as a mixture.

When the above-described solvent having a low dielectric constant is used as the solvent, salt is removed through water washing after a reaction, and then the adamantane derivative (II) can be separated through crystallization.

A reaction temperature to be ordinarily adopted is in the range of −200 to 200° C. As long as the reaction temperature is in the range, a reaction rate does not reduce, and a reaction time is not excessively long. In addition, the amount of a polymer to be produced as a by-product does not increase. The reaction temperature is in the range of preferably −200 to 100° C., or more preferably −50 to 50° C.

A reaction pressure in terms of an absolute pressure to be ordinarily adopted is in the range of 0.01 to 10 MPa. A reaction pressure in the range is economical because the reaction pressure in the range eliminates the need for a special pressure-resistant device. The reaction pressure is preferably in the range of normal pressure to 1 MPa.

A reaction time is in the range of ordinarily 1 minute to 24 hours, preferably 5 minutes to 6 hours, or more preferably 30 minutes to 6 hours.

When $R^2$ in the sulfonyl compound represented by the general formula (II) indicates a methyl group, the adamantane derivative can be separated from a by-product by: separating a reaction product from a liquid after the completion of a reaction; adding, to the reaction product, a poor solvent for a by-product polymer in the reaction product; and removing the precipitate of the by-product polymer to be produced. In that case, methanol, ethanol, diethyl ether, or the like can be used as the poor solvent, and, of those, methanol is preferable.

To be specific, water is added to the reaction after the completion of a reaction to deactivate methanesulfonyl halide. After that, the solvent is distilled off, the residue is washed, and a catalyst is removed. Next, a poor solvent for a by-product polymer in the residue, for example, methanol is added to precipitate the by-product polymer. After the precipitate has been removed by means of a method such as filtration, the poor solvent is distilled off. Next, the residue after the poor solvent has been distilled off is recrystallized by using, for example, an ether-based solvent. As a result, the target adamantane derivative (II) in which $R^2$ represents a methyl group can be obtained at a high purity.

Distillation, crystallization, column separation, or the like can be adopted for purifying a target reaction product. It is recommended that a purification method be selected depending on the properties of a product and the kind of an impurity.

The adamantane derivative (I) can be obtained by: reacting the alcohol form of the adamantane compound represented by the general formula (III) with a sulfonyl halide compound represented by the general formula (IV) to provide the adamantane derivative (II); and reacting the adamantane derivative (II) with an alcohol. Alternatively, the sulfonyl halide compound may be etherified in advance, and the resultant may be finally turned into a (meth)acrylate.

That is, a process for producing the adamantane derivative (I) includes: a step of reacting the alcohol form of the adamantane compound represented by the general formula (III) with a sulfonyloxy halide compound represented by the following general formula (IV):

where $R^2$ has the same meaning as that described above and X represents a halogen atom to provide a sulfonyloxy form represented by the following general formula (II):

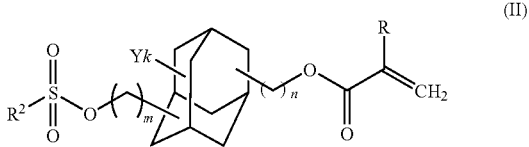

where R, R², Ys, k, m, and n each have the same meaning as that described above (a first step: a sulfonylating step); and
a step of reacting the sulfonyloxy form with an alcohol represented by the following general formula (V):

where R¹ has the same meaning as that described above to provide the target adamantane derivative (I) (a second step: an etherifying step). Hereinafter, those steps will be sequentially described.

(1) First step (Sulfonylating Step)

The sulfonyloxy halide compound to be used in the first step is similar to the above-described sulfonyl compound represented by the general formula (IV), and the sulfonyloxy form is similar to the above-described adamantane derivative (II) represented by the general formula (II). Therefore, the sulfonyloxy form (II) can be produced by means of a process similar to the above process for producing the adamantane derivative (II).

(2) Second Step (Etherifying Step)

The second step is a step of reacting the sulfonyloxy form (II) with the alcohol represented by the general formula (V) to provide the target adamantane derivative (I). Any one of methanesulfonyloxy-substituted adamantyl(meth)acrylates such as 3-methanesulfonyloxy-1-adamantyl(meth)acrylate is suitably used as the sulfonyloxy form (II).

Any one of those described above can be used as R¹ in the alcohol represented by the general formula (V); provided that a tertiary alcohol having tertiary carbon adjacent to O such as tert-butyl alcohol, tert-pentyl alcohol, or tert-hexyl alcohol is preferable from the viewpoint of usefulness of the present invention as a novel substance. A charge ratio has only to be such that the alcohol is charged in an amount in the range of 1 to 1.5 mol with respect to 1 mol of the sulfonyloxy form (II) obtained in the first step.

In this reaction, a base is generally used as a catalyst, and a solvent is used as required.

Examples of the base include: sodium amide; triethylamine; tributylamine; trioctylamine; pyridine; N,N-dimethylaniline; 1,5-diazabicyclo[4.3.0]nonene-5(DBN); 1,8-diazabicyclo[5.4.0]undecene-7(DBU); sodium hydroxide; potassium hydroxide; sodium hydride; potassium carbonate; silver oxide; sodium methoxide; and potassium t-butoxide. One kind of those catalysts may be used alone, or two or more kinds of them may be used in combination.

A solvent to be used in the etherifying step preferably has a solubility for the sulfonyloxy form (II) of 0.5 mass % or more, or desirably 5 mass % or more at a reaction temperature. It is recommended that the amount of the solvent be such that the concentration of the sulfonyloxy form (II) in a reaction mixture is 0.5 mass % or more, or desirably 5 mass % or more. At this time, the sulfonyloxy form (II), which may be in a suspended state, is desirably dissolved. In addition, moisture in the solvent is desirably removed before use. Specific examples of the solvent include: hydrocarbon-based solvents such as n-hexane and n-heptane; ether-based solvents such as diethyl ether and tetrahydrofuran; halogen-based solvents such as dichloromethane and carbon tetrachloride; dimethylsulfoxide; and N,N-dimethylsulfoxide. One kind of those solvents may be used alone, or two or more kinds of them may be used as a mixture.

A reaction temperature to be ordinarily adopted is in the range of −200 to 200° C. As long as the reaction temperature is in the range, a reaction rate does not reduce, and a reaction time is not excessively long. In addition, the amount of a polymer to be produced as a by-product does not increase. The reaction temperature is preferably in the range of 100 to 150° C.

A reaction pressure in terms of an absolute pressure to be ordinarily adopted is in the range of 0.01 to 10 MPa. A reaction pressure in the range is economical because the reaction pressure in the range eliminates the need for a special pressure-resistant device. The reaction pressure is preferably in the range of normal pressure to 10 MPa.

A reaction time is ordinarily in the range of 1 to 48 hours.

A target compound can be purified and separated by: hydrolyzing the sulfonyloxy form (II) that is unreacted with an alkaline aqueous solution such as an aqueous solution of sodium hydrogen carbonate to turn the sulfonyloxy form into an alcohol form corresponding to the general formula (III); and adsorbing the alcohol form to silica gel or the like.

The resultant compound can be identified by using, for example, gas chromatography (GC), liquid chromatography (LC), gas chromatography-mass spectrometry (GC-MS), nuclear magnetic resonance spectroscopy (NMR), infrared spectroscopy (IR), or a melting-point apparatus.

EXAMPLES

Next, the present invention will be described in more detail by way of examples. However, the present invention is not limited by these examples at all.

A value for the dielectric constant of a solvent is a numerical value according to "Solvent Pocketbook new edition" (Ohmsha, Ltd.), edited by the Society of Synthetic Organic Chemistry, Japan and "Solvent Handbook" (Koudansha Scientific) by Shozo Asahara et al., and a value for the dielectric constant of a mixed solvent (Example 10) is a numerical value calculated on the basis of an additive rule.

Example 1

Production of Adamantane Derivative (I)

Synthesis of 3-tert-pentyloxy-1-adamantyl methacrylate represented by the following structural formula:

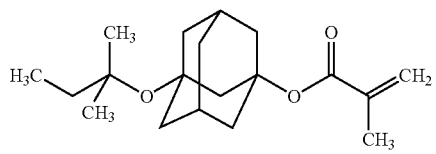

(1) Sulfonylating Step

A 2-L glass reactor was equipped with a stirring device. 118.16 g (500 mmol) of 3-hydroxy-1-adamantyl methacrylate (ADAMANTATE HM, manufactured by Idemitsu Kosan Co., Ltd.), 104.5 ml (750 mmol) of dry triethylamine, and 1 l of dry tetrahydrofuran were added to the reactor, and the mixture was stirred while the temperature of the mixture was cooled to 0° C. in an ice bath. 46.4 ml (600 mmol) of methanesulfonyl chloride were added to the mixture, and the whole was stirred for 5 minutes, followed by gas chromatography analysis. As a result, it was confirmed that 3-methanesulfonyloxy-1-adamantyl methacrylate was obtained at a degree of conversion of 92.6% and a selectivity of 99.8%. 50 ml of water were added to the resultant to deactivate unreacted methanesulfonyl chloride, and tetrahydrofuran was removed by using an evaporator. The resultant was transferred to a 2-L separating funnel, 600 ml of diethyl ether and 550 ml of water were added to the resultant twice, the mixture was washed with water twice, and a triethylamine salt and 1.01 g of a polymer were removed. 12.0 g (100 mmol) of anhydrous magnesium sulfate were added to the resultant, and the whole was dehydrated. After that, magnesium sulfate was removed by means of filtration. The resultant was evaporated in such a manner that diethyl ether would be removed, followed by gas chromatography (GC) analysis and GPC analysis. As a result, it was confirmed that 3-methanesulfonyloxy-1-adamantyl methacrylate was obtained in a yield of 156.26 g and at a purity of 91.3% (GC) or 97.8% (GPC).

(2) Etherifying Step

A 2-L glass reactor was equipped with a stirring device. The product obtained in the above item (1) was loaded into the reactor. 750.0 ml (6,849 mmol) of dry 2-methyl-2-butanol, 80.0 ml (535 mmol) of dry 1,8-diazabicyclo[5.4.0]-7-undecene (DBU), and 0.30 g (2,000 mass ppm) of methoquinone were added to the reactor, and the mixture was stirred. The temperature of an oil bath was set to 120° C., and reflux was performed for 36 hours. In addition, 0.03 g (200 mass ppm) of methoquinone was sequentially added every 6 hours. Gas chromatography analysis confirmed that a target product was obtained at a degree of conversion of 86.9% and a selectivity of 99.8%. To turn 3-methanesulfonyloxy-1-adamantyl methacrylate that had not been converted into 3-hydroxy-1-adamantyl methacrylate, 100 ml of a saturated aqueous solution of sodium hydrogen carbonate were added, and the mixture was stirred. The mixture was stirred at 60° C. for an additional 8 hours. 2-methyl-2-butanol was removed by using an evaporator. The resultant was transferred to a 2-L separating funnel, 600 ml of diethyl ether and 550 ml of water were added to the resultant twice, the mixture was washed with water twice, and a DBU salt was removed. 12.0 g (100 mmol) of anhydrous magnesium sulfate were added to the resultant, and the whole was dehydrated. After that, magnesium sulfate was removed by means of filtration. The resultant was evaporated in such a manner that diethyl ether would be removed, followed by gas chromatography analysis. As a result, it was confirmed that a target product was obtained in a yield of 149.1 g and at a purity of 80.7%. The target product was dissolved into 1 L of hexane, and the solution was filtered and decolorized by using 100 g of silica gel to which 3-hydroxy-1-adamantyl methacrylate had been adsorbed. n-hexane was removed by using an evaporator, whereby 81.0 g of a colorless, transparent liquid were obtained. Gas chromatography analysis confirmed that a target product was obtained at a purity of 99.8%. Data on each of $^1$H-NMR, $^{13}$C-NMR, and GC-MS is shown below.

Nuclear magnetic resonance analysis (NMR): CDCl$_3$ $^1$H-NMR (500 MHz): 0.85 (t, J=7.7 Hz, 3H, o); 1.21 (s, 6H, m); 1.43 (q, J=7.4 Hz, 2H, n); 1.48 (m, 2H, h or i); 1.80 (br-s, 4H, f or j); 1.85 (s, 3H, a); 1.97 (d, J=11.5 Hz, f or j); 2.08 (d, J=11.9 Hz, f or j); 2.20 (s, 2H, g); 2.25 (s, 2H, h or i); 5.43 (s, b$^1$); 5.96 (s, b$^2$), $^{13}$C-NMR (126 MHz): 8.62 (o); 18.27 (a); 29.04 (h or m); 31.39 (m or h); 35.07 (g or i or n); 37.49 (g or i or n); 40.06 (f or j); 43.90 (j or f); 48.96 (g or i or n); 73.35 (e or k or l); 76.42 (e or k or l); 81.54 (e or k or l); 124.31 (b); 137.85 (c); 166.28 (d)

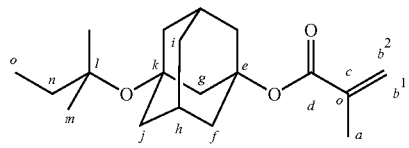

Gas chromatography mass spectroscopy analysis (GC-MS): EI 291 (M$^+$-CH$_3$, 0.05%), 219 (M$^+$-C$_5$H$_{11}$O, 100%), 133 (25.6%), 69 (98.6%), 41(26.1%)

Example 2

Production of Adamantane Derivative (I)

Synthesis of 3-(2-hydroxyethoxy)-1-adamantyl methacrylate represented by the following structural formula:

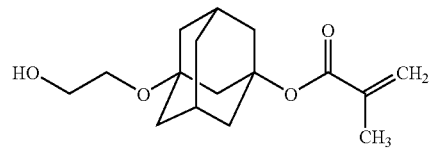

(1) Sulfonylating Step 3-methanesulfonyloxy-1-adamantyl methacrylate obtained in the same manner as in the sulfonylating step of Example 1 was added with 100 ml of diethyl ether, and the temperature of the mixture was cooled to 0° C., followed by recrystallization. As a result, 115.13 g of a white solid were obtained. Gas chromatography analysis and GPC analysis confirmed that 3-methanesulfonyloxy-1-adamantyl methacrylate was obtained at a purity of 99.1% (GC) or 98.9% (GPC).

(2) Etherifying Step

A 2-L glass reactor was equipped with a stirring device. The product obtained in the above item (1) was loaded into the reactor. 1,100.0 ml (19,725 mmol) of dry ethylene glycol and 76.0 ml (545 mmol) of dry triethylamine were added to the reactor, and the mixture was stirred. The temperature of an oil bath was set to 80° C., and heating was performed for 2 hours. Gas chromatography analysis confirmed that a target product was obtained at a degree of conversion of 99.9% and a selectivity of 99.8%. The reaction liquid was transferred to a 2-L separating funnel, and 600 ml of diethyl ether and 200 ml of water were added to the resultant so that extraction to an organic layer was performed. 700 ml of 1N dilute hydrochloric acid were added to the resultant, and the mixture was washed with water. Furthermore, 700 ml of water were added to the resultant, and the mixture was washed with water, whereby a triethylamine salt was removed. 12.0 g (100 mmol) of anhydrous magnesium sulfate were added to the resultant, and the whole was dehydrated. After that, magnesium sulfate was removed by means of filtration. The resultant was evaporated in such a manner that diethyl ether would be removed, followed by gas chromatography analysis and GPC analysis. As a result, it was confirmed that a target product was obtained in a yield of 91.96 g and at a purity of 99.5% (GC) or 99.4% (GPC). Data on each of $^1$H-NMR, $^{13}$C-NMR, GC-MS, and a melting point is shown below.

Nuclear magnetic resonance analysis (NMR): CDCl₃

¹H-NMR (500 MHz): 1.52 (d, J=12.8 Hz, 2H); 1.60 (d, J=12.8 Hz, 2H); 1.70 (d, J=11.3 Hz, 2H); 1.78 (d, J=11.3 Hz, 2H); 1.89 (s, 3H, a); 2.05 (d, J=11.3 Hz, 2H); 2.13 (d, J=11.2 Hz, 2H); 2.17 (s, 2H, g); 2.36 (br-s, 2H); 2.48 (q, J=4.0 Hz, 1H); 3.54 (t, J=4.6 Hz, 2H, l); 3.68 (q, J=5.0 Hz, 2H, m); 5.49 (q, J=1.5 Hz, b¹); 5.96(s, b²)

¹³C-NMR (127 MHz): 18.18 (a); 30.84 (h); 34.97 (i); 40.04 (f or j); 40.40 (j or f); 45.11 (g); 61.48 (l or m); 62.06 (m or l); 74.28 (k); 81.19 (e); 124.54 (b); 137.59 (c); 166.28 (d)

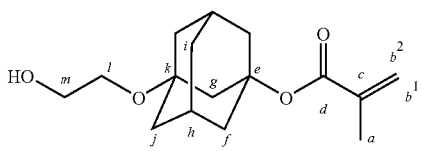

Gas chromatography mass spectroscopy analysis (GC-MS): EI 281 (M⁺+1, 0.02%), 280 (M⁺, 0.16%), 263 (0.05%), 262 (0.26%), 220 (11.0%), 219 (40.3%), 195 (8.7%), 194 (37.1%), 134 (24.0%), 133 (21.7%), 69 (100%) Melting point: DSC 50.0 to 54.5° C.

Example 3

Production of Adamantane Derivative (I)

Synthesis of 3-(2-methoxy)-1-methylethoxy methacrylate represented by the following structural formula:

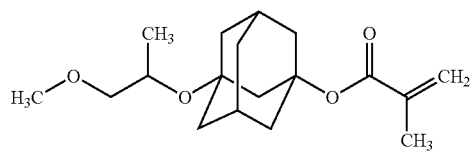

(1) Sulfonylating Step 3-methanesulfonyloxy-1-adamantyl methacrylate was obtained at a purity of 99.1% (GC) or 98.9% (GPC) in the same manner as in Example 2.

(2) Etherifying Step

A 2-L glass reactor was equipped with a stirring device. The product obtained in the above item (1) was loaded into the reactor. 1,100.0 ml (11,254 mmol) of dry 1-methoxy-2-propanol and 76.0 ml (545 mmol) of dry triethylamine were added to the reactor, and the mixture was stirred. The temperature of an oil bath was set to 80° C., and heating was performed for 2 hours. Gas chromatography analysis confirmed that a target product was obtained at a degree of conversion of 99.8% and a selectivity of 99.8%. The reaction liquid was transferred to a 2-L separating funnel, and 600 ml of diethyl ether and 200 ml of water were added to the resultant so that extraction to an organic layer was performed. 700 ml of 1N dilute hydrochloric acid were added to the resultant, and the mixture was washed with water. Furthermore, 700 ml of water were added to the resultant, and the mixture was washed with water, whereby a triethylamine salt was removed. 12.0 g (100 mmol) of anhydrous magnesium sulfate were added to the resultant, and the whole was dehydrated. After that, magnesium sulfate was removed by means of filtration.

The resultant was evaporated in such a manner that diethyl ether would be removed, followed by gas chromatography analysis and GPC analysis. As a result, it was confirmed that a target product was obtained in a yield of 106.40 g and at a purity of 99.6% (GC) or 99.5% (GPC). Data on each of ¹H-NMR, ¹³C-NMR, GC-MS, and a melting point is shown below.

Nuclear magnetic resonance analysis (NMR): CDCl₃

¹H-NMR (500 MHz): 1.21 (o); 1.48 (m, 2H, h or i); 1.80 (br-s, 4H, f or j); 1.85 (s, 3H, a); 1.97 (d, f or j); 2.08 (d, f or j); 2.20 (s, 2H, g); 3.24 (s, 3H, p); 3.34 (l); 3.50 (m); 5.43 (s, b¹); 5.96 (s, b²)

¹³C-NMR (127 MHz): 17.7 (o); 18.3 (a); 29.0 (h); 37.5 (g or i); 40.1 (f or j); 43.9 (j or f); 49.0 (g or i); 54.2 (p); 67.9 (l); 75.4 (e or k); 76.42 (e or k); 80.6 (m); 124.3 (b); 137.9 (c); 166.3 (d)

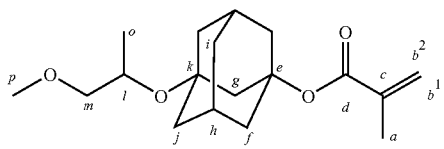

Gas chromatography mass spectroscopy analysis (GC-MS): EI 263 (M⁺-CH₂OCH₃, 11.1%), 220 (16.7%), 219 (100%), 133 (25.3%), 73 (12.2%), 69 (99.4%), 45 (10.4%), 41 (19.9%)

Example 4

Production of Adamantane Derivative (I)

Synthesis of 3-(2-cyanoethoxy)-1-adamantyl methacrylate represented by the following structural formula:

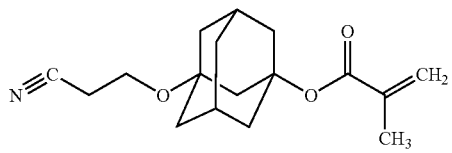

(1) Sulfonylating Step 3-methanesulfonyloxy-1-adamantyl methacrylate was obtained at a purity of 99.1% (GC) or 98.9% (GPC) in the same manner as in the Example 2.

(2) Etherifying Step

A 2-L glass reactor was equipped with a stirring device. The product obtained in the above item (1) was loaded into the reactor. 1,100.0 ml (16,110 mmol) of dry 3-hydroxypropionitrile and 76.0 ml (545 mmol) of dry triethylamine were added to the reactor, and the mixture was stirred. The temperature of an oil bath was set to 80° C., and heating was performed for 2 hours. Gas chromatography analysis confirmed that a target product was obtained at a degree of conversion of 99.8% and a selectivity of 99.8%. The reaction liquid was transferred to a 2-L separating funnel, and 600 ml of diethyl ether and 200 ml of water were added to the resultant so that extraction to an organic layer was performed. 700 ml of 1N dilute hydrochloric acid were added to the resultant, and the mixture was washed with water. Furthermore, 700 ml of water were added to the resultant, and the mixture was washed with water, whereby a triethylamine salt was removed. 12.0 g (100 mmol) of anhydrous magnesium sulfate were added to the resultant, and the whole was dehydrated. After that, magnesium sulfate was removed by means of filtration.

The resultant was evaporated in such a manner that diethyl ether would be removed, followed by gas chromatography analysis and GPC analysis. As a result, it was confirmed that a target product was obtained in a yield of 95.9 g and at a purity of 98.5% (GC) or 99.0% (GPC). Data on each of $^1$H-NMR, $^{13}$C-NMR, GC-MS, and a melting point is shown below.

Nuclear magnetic resonance analysis (NMR): CDCl$_3$ $^1$H-NMR (500 MHz): 1.48 (m, 2H, h or i); 1.80 (br-s, 4H, f or j); 1.85 (s, 3H, a); 1.97 (d, f or j); 2.08 (d, f or j); 2.20 (s, 2H, g); 2.58 (m); 3.74 (l); 5.43 (s, b$^1$); 5.96 (s, b$^2$)

$^{13}$C-NMR (127 MHz): 19.6 (m); 18.3 (a); 29.0 (h); 37.5 (g or i); 40.1 (f or j); 43.9 (j or f); 49.0 (g or i); 61.0 (l); 75.4 (e or k); 76.42 (e or k); 117.7 (n); 124.3 (b); 137.9 (c); 166.3 (d)

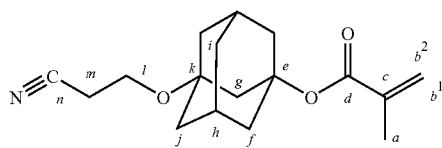

Gas chromatography mass spectroscopy analysis (GC-MS): EI

290(M$^+$+1, 0.18%), 289 (M$^+$, 1.4%), 204 (43.1%), 203 (100%), 148 (76.9%), 135 (39.3%), 92 (78.3%), 69 (88.6%), 41 (69.9%)

Example 5

Production of Adamantane Derivative (II) Involving use of Poor Solvent upon Separation Synthesis of 3-methanesulfonyloxy-1-adamantyl methacrylate represented by the following structural formula:

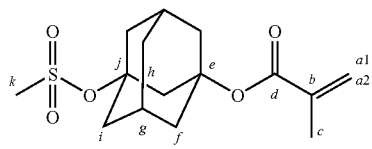

A 2-L glass reactor was equipped with a stirring device and a dropping funnel. 118.16 g (500 mmol) of 3-hydroxy-1-adamantyl methacrylate (ADAMANTATE HM, manufactured by Idemitsu Kosan Co., Ltd.), 104.5 ml (750 mmol) of dry triethylamine, and 1 L of dry tetrahydrofuran were added to the reactor, and the mixture was stirred while the temperature of the mixture was cooled to 0° C. in an ice bath. 46.4 ml (600 mmol) of methanesulfonyl chloride were dropped to the mixture over 1 hour, and the whole was stirred for an additional 1 hour, followed by gas chromatography analysis. As a result, it was confirmed that 3-hydroxy-1-adamantyl methacrylate was completely converted and a target product was obtained at a selectivity of 99.5%. 50 ml of water were added to the resultant to deactivate unreacted methanesulfonyl chloride, and tetrahydrofuran was removed by using an evaporator. The resultant was transferred to a 2-L separating funnel, 600 ml of diethyl ether and 550 ml of water were added to the resultant twice, the mixture was washed with water twice, and a triethylamine salt was removed. After diethyl ether had been removed from the resultant by using an evaporator, 300 ml of methanol were added to the remainder to precipitate a polymer, and 31.44 g of the polymer were removed by means of filtration. After methanol had been removed from the filtrate by using an evaporator, 200 ml of diethyl ether and 12.0 g (100 mmol) of anhydrous magnesium sulfate were added to the resultant, and the whole was dehydrated. After that, magnesium sulfate was removed by means of filtration. Diethyl ether was removed from the resultant by using an evaporator, followed by gas chromatography analysis and GPC analysis. As a result, it was confirmed that a target product was obtained in a yield of 115.37 g and at a purity of 98.2% (GC) or 98.7% (GPC). 50 ml of diethyl ether were added to the resultant, and the temperature of the mixture was cooled to −20° C., followed by recrystallization. As a result, 102.21 g of a white solid were obtained. Gas chromatography analysis confirmed that a target product was obtained at a purity of 98.9%.

The analyses of the compound are shown below.

Nuclear magnetic resonance analysis (NMR): CDCl$_3$ $^1$H-NMR (500 MHz): 1.55 (g); 1.85 (c); 2.04 to 2.06 (f or i); 2.13 to 2.16 (f or i); 2.18 (h); 2.39 (f or i); 2.58 (f or i); 2.97 (k); 5.47 to 5.48 (a2); 5.98 (a1)

$^{13}$C-NMR (127 MHz): 18.3 (c); 31.5 (k); 34.3 (f or h or i); 39.5 (f or h or i); 40.9 (g); 41.7 (f or h or i); 46.6 (f or h or i); 80.6 (j); 90.3 (e); 125.0 (a); 137.4 (b); 166.2 (d) Gas chromatography mass spectroscopy analysis (GC-MS): EI 315 (M$^+$+1, 2.%), 314 (M$^+$, 11.4%), 149 (78.8%), 133 (82.6%), 69 (100%)

Example 6

Production of Adamantane Derivative (II) Involving use of Organic Solvent having Low Dielectric Constant Upon Reaction A 200-mL glass reactor was equipped with a stirring device, a dropping funnel, and a temperature gauge. 10.0 g (42 mmol) of ADAMANTATE HM (manufactured by Idemitsu Kosan Co., Ltd.: 3-hydroxy-1-adamantyl methacrylate), 8.8 mL (63 mmol) of triethylamine, and 84.0 mL of toluene were added to the reactor, and the mixture was stirred while the reactor was immersed in a water bath at 25° C. 4.0 mL (50 mmol) of methanesulfonyl chloride were dropped to the mixture over 35 minutes, and the whole was stirred for an additional 25 minutes. 10 mL of water were added to the resultant to deactivate unreacted methanesulfonyl chloride. Part of the reaction liquid was taken and subjected to GPC measurement in such a manner that a production ratio between a target product and a polymer would be measured. The remaining reaction liquid was transferred to a 200-mL separating funnel, and the resultant was washed with 40 mL of water added to the resultant. After that, an organic layer was washed with 50 mL of 1-mmol/mL hydrochloric acid and then with 50 mL of water. No polymer was precipitated in the course of the liquid separating operation. 6.0 g (50 mmol) of anhydrous magnesium sulfate were added to the resultant, and the whole was dehydrated. After that, magnesium sulfate was removed by means of filtration. The filtrate was subjected to an evaporator in such a manner that toluene would be distilled off. After that, the temperature of the resultant viscous product was cooled to 0° C., followed by crystallization. After having been washed with a small amount of n-hexane, the crystal was separated by means of filtration, and was dried under reduced pressure until the amount of the crystal became constant, whereby an adamantane derivative as a target product (3-methanesulfonyloxy-1-adamantyl methacrylate) was obtained. Table 1 shows the results of: the yield (mol %) of the target product with respect to the adamantane compound as a raw material; the purity (mass %) of the target product measured by means of gas chromatography; and the production ratio (mass %) of the polymer as a result of the GPC measurement.

Example 6-1

Production of Adamantane Derivative (II) Not Involving use of Organic Solvent having Low Dielectric Constant Upon Reaction A 200-mL glass reactor was equipped with a stirring device, a dropping funnel, and a temperature gauge. 10.0 g (42 mmol) of ADAMANTATE HM (manufactured by Idemitsu Kosan Co., Ltd.: 3-hydroxy-1-adamantyl methacrylate), 8.8 mL (63 mmol) of triethylamine, and 84 mL of tetrahydrofuran were added to the reactor, and the mixture was stirred while the reactor was immersed in a water bath at 25° C. 4.0 mL (50 mmol) of methanesulfonyl chloride were dropped to the mixture over 35 minutes, and the whole was stirred for an additional 25 minutes. 10 mL of water were added to the resultant to deactivate unreacted methanesulfonyl chloride. Part of the reaction liquid was taken and subjected to GPC measurement in such a manner that a production ratio between a target product and a polymer would be measured. The remaining reaction liquid was transferred to a 300-mL separating funnel, 100 mL of diethyl ether and 40 mL of water were added to the resultant, and the mixture was washed with water. At that time, a polymer was precipitated to adhere to the separating funnel. In addition, the cock of the separating funnel was clogged with the polymer upon separation of an organic layer and an aqueous layer, so liquid separation involved time and a trouble. After that, the organic layer was washed with 50 mL of 1-mmol/mL hydrochloric acid and then with 50 mL of water. 6.0 g (50 mmol) of anhydrous magnesium sulfate were added to the resultant, and the whole was dehydrated. After that, magnesium sulfate was removed by means of filtration. The filtrate was subjected to an evaporator in such a manner that the solvent would be distilled off. After that, the temperature of the resultant viscous product was cooled to 0° C., followed by crystallization. After having been washed with a small amount of n-hexane, the crystal was separated by means of filtration, and was dried under reduced pressure until the amount of the crystal became constant, whereby a target product was obtained. Table 1 shows the results of: the yield of the target product; the purity of the target product measured by means of gas chromatography; and the production ratio of the polymer as a result of the GPC measurement.

Example 7

Production of Adamantane Derivative (II) Involving use of Organic Solvent having Low Dielectric Constant Upon Reaction A 200-mL glass reactor was equipped with a stirring device, a dropping funnel, and a temperature gauge. 10.0 g (42 mmol) of ADAMANTATE HM (manufactured by Idemitsu Kosan Co., Ltd.: 3-hydroxy-1-adamantyl methacrylate), 8.8 mL (63 mmol) of triethylamine, and 42 mL of toluene were added to the reactor, and the mixture was stirred while the temperature of the mixture was cooled to 5° C. in an ice bath. 4.0 mL (50 mmol) of methanesulfonyl chloride were dropped to the mixture over 3 minutes, and the whole was stirred for an additional 5 minutes. 10 mL of water were added to the resultant to deactivate unreacted methanesulfonyl chloride. Part of the reaction liquid was taken and subjected to GPC measurement in such a manner that a production ratio between a target product and a polymer would be measured. The remaining reaction liquid was transferred to a 200-mL separating funnel, and the resultant was washed with 40 mL of water added to the resultant. After that, an organic layer was washed with 50 mL of 1-mmol/mL hydrochloric acid and then with 50 mL of water. No polymer was precipitated in the course of the liquid separating operation. 6.0 g (50 mmol) of anhydrous magnesium sulfate were added to the resultant, and the whole was dehydrated. After that, magnesium sulfate was removed by means of filtration. The filtrate was subjected to an evaporator in such a manner that toluene would be distilled off. After that, the temperature of the resultant viscous product was cooled to 0° C., followed by crystallization. After having been washed with a small amount of n-hexane, the crystal was separated by means of filtration, and was dried under reduced pressure until the amount of the crystal became constant, whereby a target product was obtained. Table 1 shows the results of: the yield (mol %) of the target product with respect to the adamantane compound as a raw material; the purity (mass %) of the target product measured by means of gas chromatography; and the production ratio (mass %) of the polymer as a result of the GPC measurement.

Example 7-1

Production of Adamantane Derivative (II) Not Involving use of Organic Solvent having Low Dielectric Constant Upon Reaction A 200-mL glass reactor was equipped with a stirring device, a dropping funnel, and a temperature gauge. 10.0 g (42 mmol) of ADAMANTATE HM (manufactured by Idemitsu Kosan Co., Ltd.: 3-hydroxy-1-adamantyl methacrylate), 8.8 mL (63 mmol) of triethylamine, and 42 mL of tetrahydrofuran were added to the reactor, and the mixture was stirred while the temperature of the mixture was cooled to 5° C. in an ice bath. 4.0 mL (50 mmol) of methanesulfonyl chloride were dropped to the mixture over 3 minutes, and the whole was stirred for an additional 5 minutes. 10 mL of water were added to the resultant to deactivate unreacted methanesulfonyl chloride. Part of the reaction liquid was taken and subjected to GPC measurement in such a manner that a production ratio between a target product and a polymer would be measured. The remaining reaction liquid was transferred to a 300-mL separating funnel, 100 mL of diethyl ether and 40 mL of water were added to the resultant, and the mixture was washed with water. At that time, a polymer was precipitated to adhere to the separating funnel. After that, the organic layer was washed with 50 mL of 1-mmol/mL hydrochloric acid and then with 50 mL of water. 6.0 g (50 mmol) of anhydrous magnesium sulfate were added to the resultant, and the whole was dehydrated. After that, magnesium sulfate was removed by means of filtration. The filtrate was subjected to an evaporator in such a manner that the solvent would be distilled off. After that, the temperature of the resultant viscous product was cooled to 0° C., followed by crystallization. After having been washed with a small amount of n-hexane, the crystal was separated by means of filtration, and was dried under reduced pressure until the amount of the crystal became constant, whereby a target product was obtained. Table 1 shows the results of: the yield of the target product; the purity of the target product measured by means of gas chromatography; and the production ratio of the polymer as a result of the GPC measurement.

Example 7-2

Production of Adamantane Derivative (II) Not Involving use of Organic Solvent having Low Dielectric Constant Upon Reaction A target product was obtained in the same manner as in Example 7 except that toluene in Example 7 was changed to methylene chloride. A polymer was precipitated in the course of liquid separation. Table 1 shows the results of: the yield of the target product; the purity of the target product measured by means of gas chromatography; and the production ratio of the polymer as a result of the GPC measurement.

Example 8

Production of Adamantane Derivative (II) Involving use of Organic Solvent having Low Dielectric Constant Upon Reaction A target product was obtained in the same manner as in Example 7 except that the amount of toluene, which had been 42 mL in Example 7, was changed to 84 mL. No polymer was precipitated in the course of liquid separation. Table 1 shows the results of: the yield of the target product; the purity of the target product measured by means of gas chromatography; and the production ratio of the polymer as a result of the GPC measurement.

Example 9

Production of Adamantane Derivative (II) Involving use of Organic Solvent having Low Dielectric Constant Upon Reaction A target product was obtained in the same manner as in Example 7 except that the amount of toluene was changed to ethylene acetate. No polymer was precipitated in the course of liquid separation. Table 1 shows the results of: the yield of the target product; the purity of the target product measured by means of gas chromatography; and the production ratio of the polymer as a result of the GPC measurement.

Example 10

Production of Adamantane Derivative (II) Involving use of Organic Solvent having Low Dielectric Constant Upon Reaction A target product was obtained in the same manner as in Example 7 except that the amount of toluene was changed to a mixed solvent with 22 mL of cyclohexane and 22 mL of tetrahydrofuran. No polymer was precipitated in the course of liquid separation. Table 1 shows the results of: the yield of the target product; the purity of the target product measured by means of gas chromatography; and the production ratio of the polymer as a result of the GPC measurement.

TABLE 1

|  | Example 6 | Example 6-1 | Example 7 | Example 7-1 | Example 7-2 | Example 8 | Example 9 | Example 10 |
|---|---|---|---|---|---|---|---|---|
| Solvent usage (mL) | | | | | | | | |
| Toluene | 84 | | 42 | | | 84 | | |
| Cyclohexane | | | | | | | | 22 |
| Ethyl acetate | | | | | | | 42 | |
| Tetrahydrofuran | | 84 | | 42 | | | | 22 |
| Methylene chloride | | | | | 42 | | | |
| Dielectric constant of solvent | 2.2 | 8.2 | 2.2 | 8.2 | 9.1 | 2.2 | 6.0 | 5.1 |
| Reaction method | | | | | | | | |
| Bath temperature (° C.) | 25 | 25 | 5 | 5 | 5 | 5 | 5 | 5 |
| Drop time (min) | 35 | 35 | 3 | 3 | 3 | 3 | 3 | 3 |
| Time for subsequent stirring (min) | 25 | 25 | 5 | 5 | 5 | 5 | 5 | 5 |
| Adamantane derivative (II) | | | | | | | | |
| Yield (mol %) | 95 | 66 | 94 | 90 | 86 | 96 | 95 | 95 |
| Purity (mass %) | 99.0 | 98.3 | 99.1 | 97.7 | 94.8 | 99.4 | 98.9 | 98.9 |
| Production ratio of polymer | 0.4 | 28.8 | 0.6 | 4.4 | 8.3 | 0.3 | 2.2 | 1.9 |

INDUSTRIAL APPLICABILITY

Each of the adamantane derivative (I) of the present invention represented by the general formula (I) and the adamantane derivative (II) of the present invention represented by the general formula (II) is a novel adamantyl(meth)acrylate compound, and is useful as a monomer for a functional resin such as a photosensitive resin in the field of photolithography.

The adamantane derivative (I) of the present invention is expected to exert an alleviating effect on surface roughness after exposure (LER: irregularities appearing on the side surface of a resist, LWR: waviness when wiring is seen from directly above) and an improving effect on, for example, the temperature dependence of PEB (a heat treatment for diffusing an acid generated by exposure).

In addition, compatibility between the adamantane derivative (II) of the present invention and a photoacid generator (PAG) as one component of a resist agent mixed liquid is considered to improve. As a result, a uniform film can be formed, and the film is expected to exert an alleviating effect on surface roughness after exposure (LER: irregularities appearing on the side surface of a resist, LWR: waviness when wiring is seen from directly above).

Furthermore, each of the adamantane derivative (I) and the adamantane derivative (II) can be produced in high yield by means of the process for producing each of those adamantane derivatives of the present invention. In particular, in the process for producing the adamantane derivative (II) involving a reaction in an organic solvent having a dielectric constant at 20° C. of 8 or less, the production of a polymer can be suppressed, so an improvement in handleability is achieved, and the derivative can be produced efficiently and industrially advantageously.

The invention claimed is:

1. An adamantane derivative, characterized by comprising a structure represented by a general formula (II):

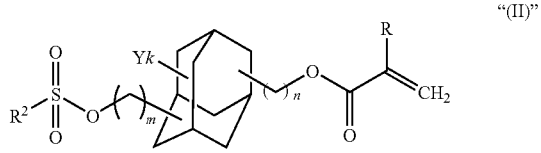

"(II)"

where R represents a hydrogen atom, a methyl group, or a $CF_3$ group, $R^2$ represents an alkyl group having 1 to 10 carbon atoms, a phenyl group, an alkylphenyl group, or a $CF_3$ group, Ys each represent an alkyl group having 1 to 10 carbon atoms, a halogen atom, or a hydroxyl group, or two Ys are coupled to form =O, and multiple Ys may be identical to or different from each other, k represents an integer of 0 to 14, and m and n each independently represent an integer of 0 to 4.

2. The adamantane derivative according to claim 1, wherein $R^2$ represents a methyl group.

3. A process for producing an adamantane derivative having a structure represented by the general formula (II):

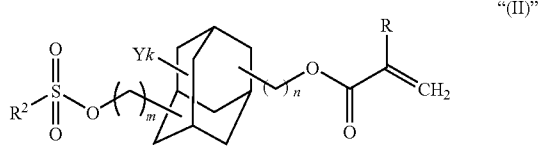

"(II)"

where R represents a hydrogen atom, a methyl group, or a $CF_3$ group, $R^2$ represents an alkyl group having 1 to 10 carbon atoms, a phenyl group, an alkylphenyl group, or a $CF_3$ group, Ys each represent an alkyl group having 1 to 10 carbon atoms, a halogen atom, or a hydroxyl group, or two Ys are coupled to form =O, and multiple Ys may be identical to or different from each other, k represents an integer of 0 to 14, and m and n each independently represent an integer of 0 to 4, the process being characterized by comprising reacting an alcohol form of an adamantane compound represented by a general formula (III):

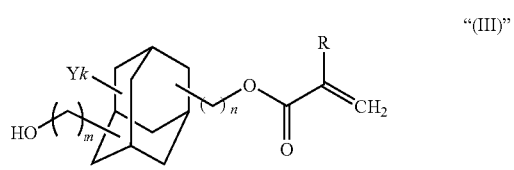

"(III)"

where R, Ys, k, m, and n each have the same meaning as that described above, with a sulfonyl compound represented by a general formula (IV):

"(IV)"

where $R^2$ represents an alkyl group having 1 to 10 carbon atoms, a phenyl group, an alkylphenyl group, or a $CF_3$ group, and X represents a hydroxyl group or a halogen atom.

4. The process for producing an adamantane derivative according to claim 3, wherein the alcohol form of the adamantane compound represented by the general formula (III) and the sulfonyl compound represented by the general formula (IV) are reacted with each other in an organic solvent having a dielectric constant at 20° C. of 8 or less.

5. The process for producing an adamantane derivative according to claim 3, wherein the sulfonyl compound represented by the general formula (IV) comprises methanesulfonyl halide.

6. The process for producing an adamantane derivative according to claim 3, wherein, after the alcohol form of the adamantane compound represented by the general formula (III) and the sulfonyl compound represented by the general formula (IV) have been reacted with each other, a reaction product is separated from a liquid after completion of the reaction, a poor solvent for a by-product polymer in the reaction product is added to the reaction product, and a precipitate of the by-product polymer to be produced is removed.

7. The process for producing an adamantane derivative according to claim 6, wherein the poor solvent for the by-product polymer comprises methanol.

* * * * *